United States Patent [19]

Heaney

[11] 4,329,982
[45] May 18, 1982

[54] ORTHOTIC FOOT ASSIST APPARATUS

[76] Inventor: Audrey C. Heaney, 200 Lexington Ave., Oyster Bay, N.Y. 11771

[21] Appl. No.: 198,063

[22] Filed: Oct. 17, 1980

[51] Int. Cl.³ .............................................. A61F 3/00
[52] U.S. Cl. .................................................. 128/80 E
[58] Field of Search ............... 128/80 R, 80 E, 80 H, 128/80 F

[56] References Cited

U.S. PATENT DOCUMENTS

| | | | |
|---|---|---|---|
| 1,356,327 | 10/1920 | Winiarski | 128/80 E |
| 1,598,504 | 8/1926 | Pierce et al. | 128/80 H |
| 3,805,773 | 4/1974 | Sichau | 128/80 E |

FOREIGN PATENT DOCUMENTS

| | | | |
|---|---|---|---|
| 332342 | 3/1919 | Fed. Rep. of Germany | 128/80 E |
| 548527 | 3/1932 | Fed. Rep. of Germany | 128/80 E |
| 593057 | 8/1977 | Switzerland | 128/80 E |

*Primary Examiner*—John D. Yasko
*Attorney, Agent, or Firm*—Scully, Scott, Murphy & Presser

[57] ABSTRACT

An apparatus for assisting a person having a foot-drop type disability is provided which includes a leg attachment member, an elastomeric support strap, and a latch and loop for attaching the support strap to the wearer's foot. The elastomeric support strap is secured to both the leg attachment member and one of the latch or loop. When the apparatus is in use, the elastomeric support strap contracts to raise the wearer's foot during the time period that the wearer is not forcibly extending the strap by downwardly extending his or her foot.

4 Claims, 2 Drawing Figures

ORTHOTIC FOOT ASSIST APPARATUS

BACKGROUND OF THE INVENTION

1. Field of the Invention

This invention relates to an apparatus designed to assist a person having a foot-drop type of disability.

Persons who have sustained a stroke or suffer from diseases such as multiple sclerosis, post-polio sequelae, et al., generally incur certain neuromuscular pathological conditions because of damage to the nerves which innervate the muscles involved. This damage occurs centrally in the brain and/or spinal cord, or locally to peripheral nerves, such as those found in the leg, resulting in paralysis or partial paralysis in varying degrees of severity to different parts of the body. Generally, the distal joints are proportionately weaker than the more proximal joints (proximal meaning close to the midpoint of the body). Therefore, hip and knee extension (straightening) muscles while weakened with, for instance, a one-sided paralysis (commonly occuring in stroke victims), are, nevertheless, usually adequate to support the body by maintaining hip and knee extension sufficient for a limited amount of standing and walking which is usually feasible because the second leg is normal, and the person most often will have the added support and balance provided by a cane. As a result, a joint such as the ankle is frequently wholly or partially debilitated while the hip and/or knee remain relatively less affected.

Paralysis, in any degree, of the ankle and the mid-tarsal joint (just distal to the ankle), commonly known as foot-drop, present greater problems because of the independent movement required of them in walking. Ankle motions are dorsi-flexion (up) and plantar flexion (down), and mid-tarsal joint motions are inversion (inward turning) and eversion (outside edge of the foot turned up). Paralysis or partial paralysis for any of the reasons described herein usually impair the ankle and mid-tarsal joint such that dorsi-flexion and eversion are weaker than plantar flexion and inversion. Both dorsi-flexion and eversion, however, are required for walking so that the foot and toes do not drag. Therefore, a need exists for a foot-assist mechanism which selectively provides support for the foot by compensating for the affected muscles while allowing the functioning muscles or portions thereof to continue to operate to their fullest extent.

2. The Prior Art

A number of devices have been provided to date to alleviate foot-drop which includes short-leg braces having metal uprights, metal stirrups, molded calf cups, etc. These devices suffer disadvantages such as their weight, which taxes the strength of the leg, and their bulkiness, which tends to cause injury to the opposite ankle. More recently, U.S. Pat. No. 3,986,501 to Schad shows a foot-drop apparatus having a rigid vertical member curved and arched to conform to the rear of the calf of the human leg (the bottom of the vertical member having a cup-like shape to conform to the heel of the foot without extending under the heel) and a V-strap member connected at the top of the vertical member for the purpose of insertion at the shoe near the dorsum portion of the foot for lifting the dorsum of the foot when the heel is raised.

All of the above devices, however, are static in nature in that they maintain the foot in a relatively fixed position in relation to the leg (which is never greater than 90°) at all times so that the entire lower leg from calf to toes moves en masse as a rigid structure being propelled and supported by the person's knee, hip and spine, thereby producing an awkward gait. Since the muscles involved in plantar flexion or straightening the ankle (the extreme of which is standing on the toes) are relatively much less affected in the disabilities described above, these devices actually immobilize working muscles to a degree, thereby causing their atrophy or earlier degeneration.

Also, the devices incorporating rigid members such as the device shown in the Schad '501 patent lose conformity with the wearer's leg due to muscle atrophy, slide up and down and/or rub against the leg, and cause excessive perspiration thus contributing to the discomfort of the wearer. Moreover, such irritation to the lower extremity of a person, who may have experienced some loss of sensory perception in the leg as a concomitant result of the debilitating condition, is likely to cause more severe discomfitures such as blistering, decubitus ulcers, etc.

It is, therefore, an object of the present invention to assist a person having a foot-drop type disability by providing a device which will aid the functioning of those muscles directly effected by a disabling condition, such as those described hereinbefore, but which allows full range of motion of the foot and usage of those muscles either not effected or only partially effected.

Commensurately, it is an object of this invention to provide a foot-drop assist apparatus which eliminates the discomfiture described above relating to static type foot-drop assist devices and the periodic adjusting or replacement normally associated with such devices.

Finally, it is intended to provide a foot-drop assist apparatus which is lightweight, relatively inconspicuous, easy to use, and very inexpensive to make and maintain.

SUMMARY OF THE INVENTION

In accordance with the present invention, there is provided an apparatus for assisting a person having a foot-drop type disability which includes a leg attachment member, an elastomeric support strap, and a means for attaching the support strap to the wearer's foot. The elastomeric support strap is secured to both the leg attachment member and the means for attaching the support strap to the wearer's foot. When the apparatus is in use, the elastomeric support strap contracts to raise the wearer's foot during the time period that the wearer is not forcibly extending the strap by downwardly extending his or her foot. Preferably, the leg attachment member is an adjustable band secured to the wearer's lower leg on or immediately above the calf and is made of a width of fabric which is bifurcated at one end to form two narrower strips each of which have an adjustable closure device so that either side of the adjustable band may be selectively adjusted to conform to the wearer's leg.

In a preferred embodiment of the present invention the means for attaching to the wearer's foot is essentially a latch and loop, one of which is arranged on the wearer'shoe at a point generally on the forward portion of the shoe and on the lateral (outside) side of the shoe. The cooperating counterpart of the attaching means is secured to the elastomeric strap which, in turn, is secured to the leg attachment member at a point on the lateral side of the leg so that when the strap operates to raise the foot, eversion (outward turning) is effected.

As a result of this invention, a person having a foot-drop type disability may now use the relatively uneffected muscles without hindrance or discomfort to their fullest extent, e.g. by extending the foot (plantar flexion), while at the same time enjoying the benefits of a convenient selectively-active assist mechanism which will help them to walk normally. Inasmuch as the muscles used to raise the foot (dorsi-flexion) and turn it outward (eversion), both of which are required in walking, are nearly always affected in those persons suffering residual paralysis as a result of a stroke, the present invention is particularly useful to stroke victims, especially since the degree of recovery from paralysis caused by stroke very often depends on the extent to which such victims use muscles having normal active contractility.

Furthermore, the present foot-drop assist apparatus actually delays the speed with which progressively debilitating diseases such as multiple sclerosis incapacitates its victim by permitting the viable muscles to remain fully active until they are directly effected by the damaging disease.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
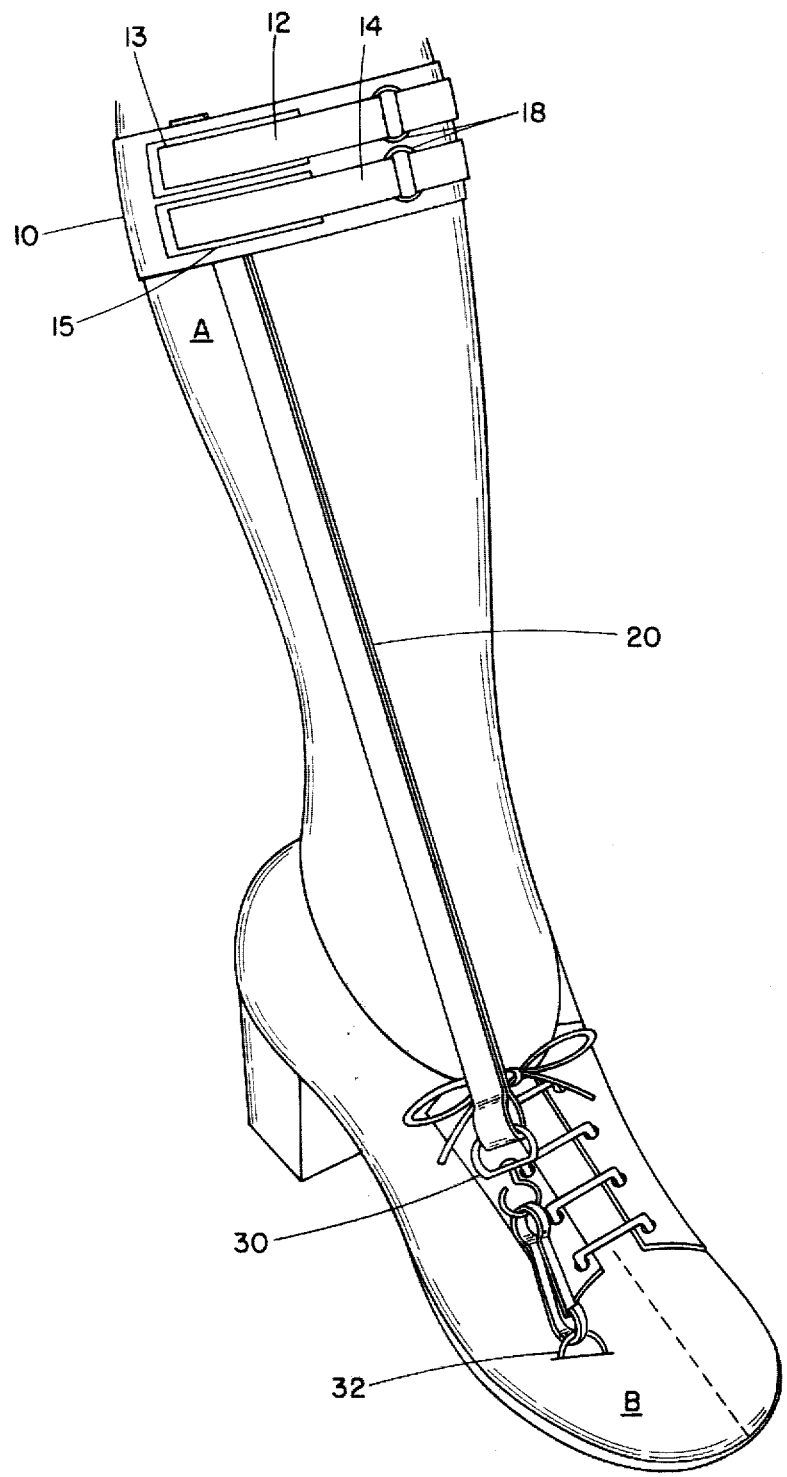
FIG. 1 is a perspective view of the apparatus of the present invention, showing it worn on the lower leg.

Referring to the figures a leg attachment band 10 is affixed to the leg at a point somewhere on or immediately above the calf of the wearer, generally designated as A. In order to better conform the leg attachment band 10 to the shape of the leg, two narrow strips 12 and 14 are provided in the preferred embodiment, each of which may be individually adjusted by passing them through rings 18—which are secured to the leg attachment band 10—to the desired lengths. Commensurate with this particular embodiment the narrow strips 12 and 14 may be provided with closure devices 13 and 15, such as strips of adhering cloth sold under the trademark VELCRO. This entire leg attachment band 10 can be easily prepared, for example, from a 2" width of cotton fabric which is bifurcated at one end to form the individual narrow strips 12 and 14.

Elastomeric support strap 20 is secured to leg attachment band 10 so that, in the preferred embodiment, the top of support strap 20 is positioned at a point generally in the front and on the lateral side (outside) of the leg while at the same time allowing adjustable strips 12 and 14 to be located, conveniently, generally on the front half of the leg. As the lower end of support strap 20 is connected one member of a means for attaching the support strap to the wearer's foot, such as a swivel latch 30, which cooperates with another member of a means for attaching such as a loop 32 affixed to the wearer's shoe. It is particularly advantageous that the loop 32 be located on the front part of the shoe and generally on the lateral side (outside) designated generally as the portion B of the wearer's shoe.

Figure 2:
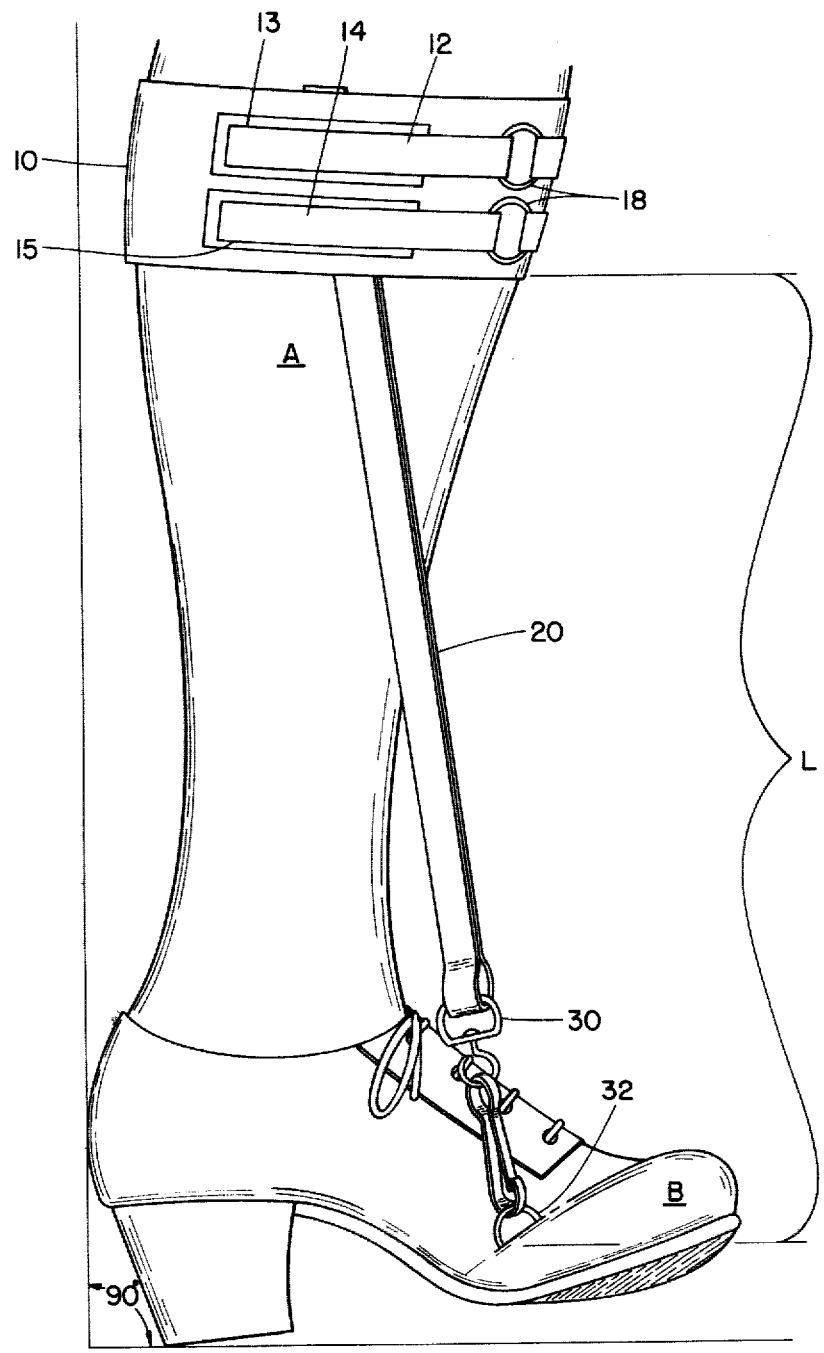
FIG. 2 shows the present apparatus as it operates to raise the foot.

The overall length "1" of the support strap 20, swivel latch 30, and loop 32 is such that when the strap 20 is in the contracted, completely unextended condition, the foot must be raised to form less than a 90° angle with the leg (see FIG. 2). In this way the support strap will contract to raise the foot in order to clear the ground when the wearer is not forcibly extending the support strap—i.e. while the person lifts his or her foot from the ground to take a step forward. The positioning of the latch 30 and loop 32 on the lateral side of the foot, according to the preferred embodiment, also effects eversion (the outward turning of the foot) which is the type of motion a person makes during normal walking.

In addition to the beneficial physical and therapeutic features of this invention, it is also very inexpensive to make and can be maintained quite simply by washing it as one would any item of clothing. Finally, the adjustable quality of leg attachment band 10 eliminates the need to continually reform and/or replace the mechanism because of lack of conformity to the user's changing musculature.

While there has been described what is presently believed to be the preferred embodiment of the invention, those skilled in the art will realize that changes and modifications may be made thereto without departing from the spirit of the invention, and it is intended to claim all such changes and modifications as fall within the tue scope of the invention.

I claim:

1. An apparatus for assisting a person having a foot-drop type disability, comprising; a leg attachment member; an elastomeric support strap secured to said leg attachment member; and a shoe with a cooperating means for attaching said support strap to said shoe, said means for attaching further comprising a loop and a latch, one of said loop and said latch being secured to said shoe of the wearer at a point generally on the forward portion of said shoe and on the lateral side of said shoe, while the other of said loop and said latch is secured to said elastomeric support strap which, in turn, is secured to said leg attachment means at a point on the lateral side of the wearer's leg so that when said apparatus is worn said strap contracts to raise the wearer's foot during the time said wearer is not forcibly extending said strap by the downward extension of said foot and simultaneously effects eversion when said strap operates to raise said foot.

2. An apparatus as described in claim 1, wherein said leg attachment member comprises an adjustable band securable to the leg at a point on the lower leg on or immediately above the calf.

3. An apparatus as described in claim 2 wherein said adjustable band comprises a width of fabric having one bifurcated end forming two narrower strips; and an adjustable closure device affixed on each of said strips and cooperating therewith so that either side of said band is selectively adjustable to conform to the wearer's leg.

4. An apparatus as described in claim 3, wherein said adjustable closure devices comprise lengths of adhesive cloth attached to said adjustable band and said strips so that said lengths adhere cooperatively to hold said band on the wearer's leg.

* * * * *